Figure 1:
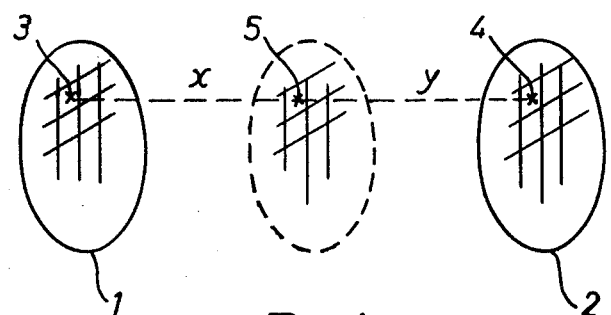

United States Patent [19]

Hounsfield

[11] 4,029,948

[45] June 14, 1977

[54] RADIOGRAPHY

[75] Inventor: Godfrey Newbold Hounsfield, Newark, England

[73] Assignee: E M I Limited, Hayes, England

[22] Filed: July 10, 1975

[21] Appl. No.: 594,786

[30] Foreign Application Priority Data

July 11, 1974 United Kingdom ............ 30712/74

[52] U.S. Cl. .................... 235/151.3; 250/445 T; 358/111
[51] Int. Cl.² .................. G01N 23/06; G01T 1/166
[58] Field of Search .......... 235/151.3, 151.11, 152; 250/336, 362, 363, 445 T, 445 R; 178/DIG. 5, DIG. 35; 346/33 ME, 33 B; 128/2 A; 444/1

[56] References Cited
UNITED STATES PATENTS

| 3,582,651 | 6/1971  | Siedband        | 178/7.8 X    |
|-----------|---------|-----------------|--------------|
| 3,679,823 | 7/1972  | Corrigan, Jr.   | 178/DIG. 5 X |
| 3,778,614 | 12/1973 | Hounsfield      | 250/362      |
| 3,818,220 | 6/1974  | Richards        | 250/445 T X  |
| 3,894,181 | 7/1975  | Mistretta et al.| 178/DIG. 5 X |
| 3,944,833 | 3/1976  | Hounsfield      | 250/367      |
| 3,950,613 | 4/1976  | Macovski        | 178/DIG. 5 X |

*Primary Examiner*—Edward J. Wise
*Attorney, Agent, or Firm*—Fleit & Jacobson

[57] ABSTRACT

In an apparatus for displaying representation of body sections derived, for example, from a diagnostic X-ray apparatus a further representation is provided for another body section by interpolation between the derived representations. The data for elements of the derived representation are stored and those relating to corresponding elements are withdrawn simultaneously for the interpolation to provide the corresponding element of the further representation. Any of the representations may be displayed individually or they may be displayed successively in a sequence relating to their position in the body.

5 Claims, 4 Drawing Figures

RADIOGRAPHY

The present invention relates to apparatus for displaying a representation of body sections for use, for example, in diagnostic X-ray apparatus and it relates especially to the display of representations between those derived directly from the said apparatus.

It has been disclosed, for example in U.S. patent specification No. 3,778,614, that it is possible by radiographic techniques to produce representations which denote the absorption (or transmission) co-efficients of each of the elements of a two-dimensional array of elements notionally delineated in a cross-section of a body. In the event that two or more such representations are available in respect of spaced cross-sections of the body, it has now been discovered that a further representation, indicative of a selected part of the body between said cross-sections can be produced.

According to the invention there is provided an apparatus for displaying a representation of body sections for use, for example, in diagnostic X-ray apparatus including storage means for storing data signals representing the absorption coefficients of elements of two-dimensional spaced arrays of elements notionally delineated in respective spaced cross-sections of the body, means for weighting data or corresponding elements of said first mentioned arrays according to predetermined interpolating functions to derive data signals repesenting coefficients for corresponding elements of another array of elements notionally delineated in another cross-section of said body and means for displaying a representation either of said first mentioned body sections or said other body section.

Figure 2:
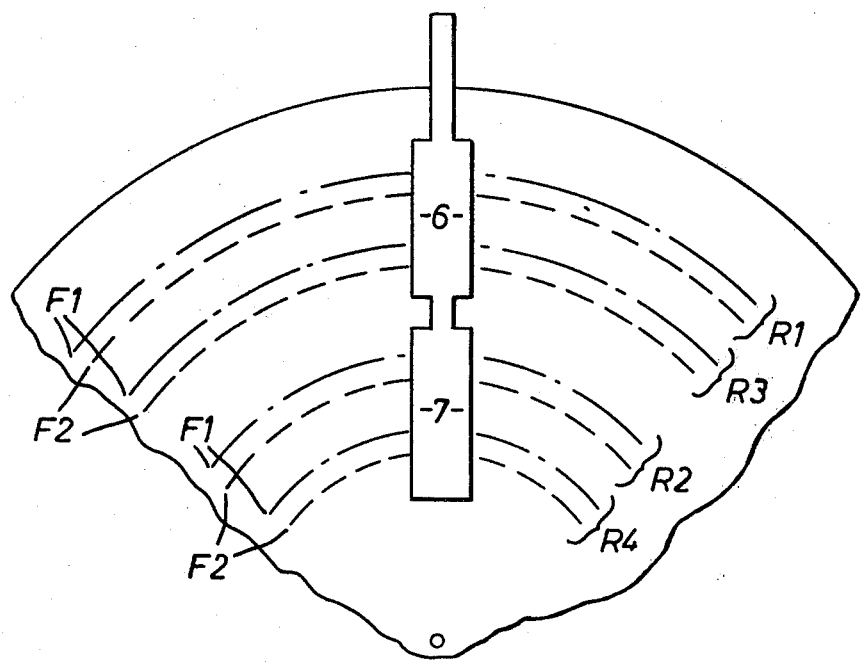
Figure 3:
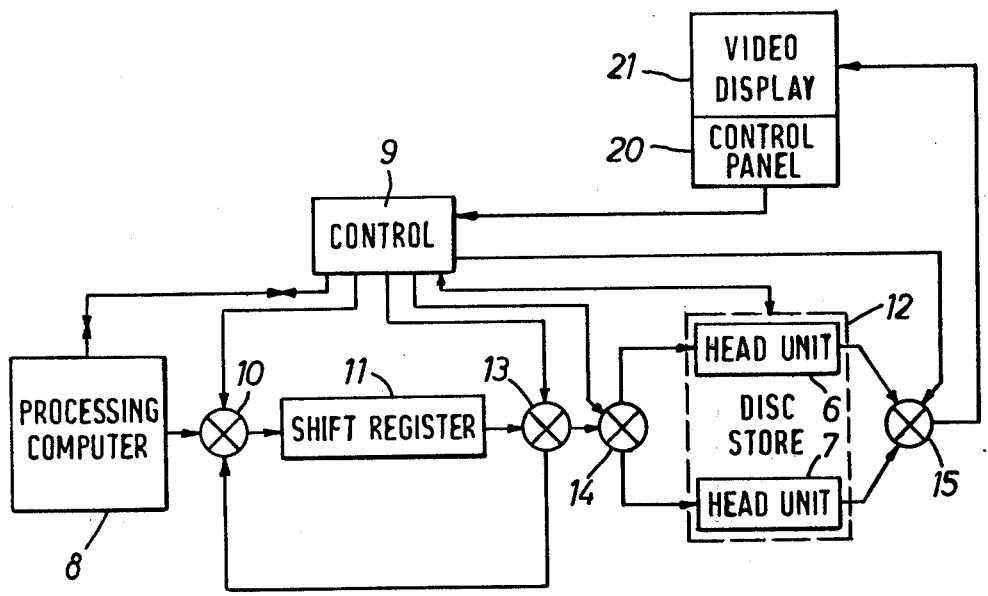
Figure 4:
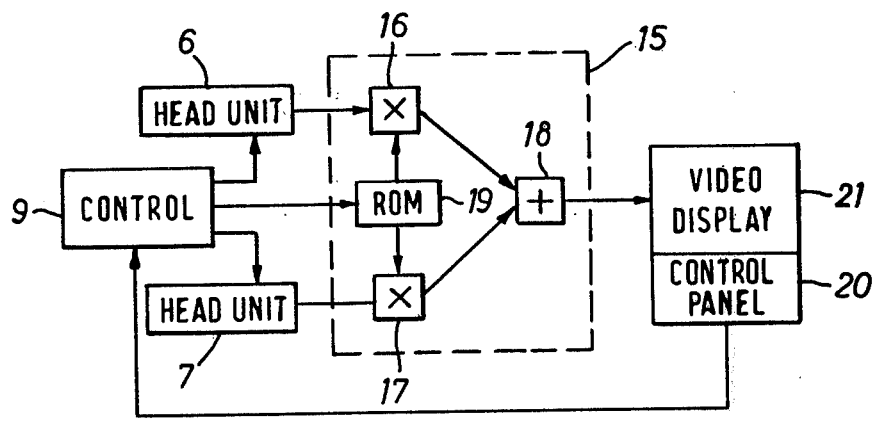

In order that the invention may be clearly understood and readily carried into effect examples thereof will now be described with reference to the accompanying drawings of which:

FIG. 1 represents schematically two representations relating to spaced portions of the body and, in broken outline, a representation of part of the body between the two portions, FIG. 2 illustrates the manner of organising absorption data relating to several such portions on a video disc, FIG. 3 shows in block diagrammatic form a circuit incorporating the invention and, FIG. 4 shows a weighting circuit suitable for use with the circuit of FIG. 3.

Referring to FIG. 1, the representation relating to the first of said portions is indicated by the reference numeral 1. The various elements are indicated by meshes, although for convenience the elements are shown on a much larger scale than they assume in practice. The representation of the second portion of the body is shown at 2. The two representations will be considered to be adjacent although they are not necessarily contiguous. Corresponding elements in the two representations 1 and 2 are shown at 3 and 4 respectively, and the perpendicular distance measured between the two representations is $x + y$. If it is desired to produce a representation of that part of the body which lies between the portions indicated by representations 1 and 2 and located at a distance $x$ from representation 1 and $y$ from representation 2, then the value of the absorption coefficients of each element of the new representation can be interpolated in the following manner.

The element 5 in the new representation, which corresponds in position to the elements, 3 and 4 in representations 1 and 2, is allocated a coefficient by means of the following formula $$A_1 \frac{(y)}{(x+y)} + A_2 \frac{(x)}{(x+y)}$$

where $A_1$ and $A_2$ represent the absorption coefficients of the mesh elements 3 and 4 respectively and $$\left(\frac{x}{x+y}\right) \text{ and } \left(\frac{y}{x+y}\right)$$

are weighting factors.

The position of the interpolated representation between the representations 1 and 2 can be smoothly adjusted by varying the ratio between $x$ and $y$ and can also be continued through either of the representations, provided that a representation is available on either side of the representaton is question. The position of the interpolated representation can be coupled mechanically to a position control knob so that it can be made to apparently change its position in the direction at right angles to the representations.

In a practical embodiment of the invention the apparatus is arranged to provide a single new representation substantially at the mid position between each pair of the original representations. In the notation given hereinbefore, that means that $x = y$ so that the new repesentation is given by elements which have absorption coefficents such as $A_1/2 + A_2/2$. It will be understood, however, that other such relationships may be used to apportion the absorption data.

In this example the X-ray apparatus obtains data for up to eight different planar slices through the body thus providing, after suitable processing by methods such as that disclosed in U.S. Pat. No. 3,924,129 eight representations, R1 to R8, for display. An interpolated representation is provided between each of these derived representations.

The x - ray apparatus provides each representation as a television type field but with 320 active lines as opposed to the television display used which has 280 active lines. For the purpose of corresponding with the latter the first and last twenty lines of the representation may be discarded or the required 280 lines may be derived from the available 320 lines by any suitable means. The complete representation is also repeated to give a television picture, having two identical fields, which is completely compatible with the display.

The pictures, each being for one representation, are stored on two circumferential tracks, one for each field, of a video disc store. The store used in this example has sixteen tracks, each with its own recording and reproducing head, in each of two zones which have independent input/output channels. A suitable store having such a specification is the PPL 104–1–2 video store manufactured by Process Peripherals Ltd. The arrangement of the data as the disc is shown in FIG. 2 on which for clarity only eight tracks are shown, four for each of two recording head units 6 and 7. The tracks relating to the heads of unit 6 are for two representations R1 and R3 and those relating to unit 7 are for intervening representations R2 and R4. In generaly data for R1, R3, R5 and R7 are stored on one set of tracks and for intervening slices R2, R4, R6 and R8 on the other. The positions of tracks relating to field F1 of each picture are shown by chain dotted lines and those for the other fieldd F2 by dashed lines.

The data are applied to their respective tracks, as will be explained hereinafter, and may be withdrawn as required via either or both of the independent output channels of head unit 6 and head unit 7. It will be appreciated that, since these head units do correspond to independent chanels and because of the interlaced nature of the track allocations, data for adjacent slices may be withdrawn smultaneously for interpolation as described hereinbefore. It will be understood also that after each revolution of the disc the picture being derived may be repeated or changed as desired.

The circuit is shown in block diagrammatic form in FIG. 3. The data for each representation is supplied by a processing computer 8, which may be as described in the aforesaid U.S. Pat. No. 392,4128 under the control of a control computer 9 which determines the required action in known manner according to input instructions from an operator at control panel 20. The data appear at the processing computer at a rate incompatible with the television rate and are to be applied to the disc store in units of one line of the picture. The control computer 9 applies the data via a gate 10 to a shift register 11. It will be understood that the parameters of the operation are known in advance by the computer 9 which merely requires information from processing computer 8 to indicate the completion of each line and field of the representation.

As mentioned hereinbefore, the data are applied in units of one line. The data are initially stored in shift register 11 until the disc store, indicated by the broken outline at 12, indicates that the start location of the respective field is available. All complete lines in register 12 are then recorded via gates 13 and 14. Up to eight complete lines can, in this example, be provided by the processing in one revolution of the disc and this is therefore the maximum storage required of the shift register 11. Any partial lines stored in shift register 11 at that time are discarded and re-supplied later by computer 8 for reasons which will become clear. The data from shift register 11 are applied to the input/output channel of head unit 6 or 7 by gate 14, in response to commands from control 9, according to the particular representation being generated. This is according to the scheme outlined in relation to FIG. 2. The disc store 12 is instructed to apply the data to the track of field F1 for that picture. At the same time gate 13, in response to control 9, recirculates these lines to register 11 via gate 10 from which they are again applied to the disc store at the corresponding locations of field F2 of the same picture. On the second ocassion they are not recirculated by gate 13 and the computer 8 is instructed to recommence supplying data at the start of the next complete line. This data is in turn recorded when the location for the start of that line is available and the cycle repeated until the two identical fields of the entire picture are recorded. It will be understood that, if desired, only one of these identical fields need be recorded and the other could be generated, with appropriate delays, immediately before display.

This sequence is repeated for the pictures of each of the constructed representations until each is in store. It will be noted that the thirty two tracks of the disc store can hold sixteen such pictures. This facility is used to store a second eight pictures of the same representation. These are however modified by the computer 8 according to various parameters, such as for example the application of a "window" of maximum and minimum levels, in response to operator controls after viewing of the original pictures.

For display a picture may be provided by the disc store and applied to a television standard display 21 via a gate circuit 15. Display 21, which may be a conventional video monitor is situated together with the operators control panel 20. Circuit 15 is arranged to pass a single picture on either of its inputs from head units 6 and 7 or to combine two outputs provided by those units simultaneously according to the relationship given hereinbefore. By this means any of the derived representations or interpolated values between them may be displayed. Alternatively, by changing tracks on the video disc at an appropriate rate, the circuit can display adjacent slices in the sequence of their positions in the body e.g.

$$R_1, \frac{R_1 + R_2}{2}, R_2, \frac{R_2 + R_3}{2}$$

etc.

In this manner an effective movement through the body, can be provided at the display, emphasising features which are continuous through all the examined slices.

Circuit 15 may if desired take the form shown in FIG. 4. In that circuit the picture data derived from the disc store are multiplied in multipliers 16 and 17 by the factors $x/(x+y)$ and $y/(x+y)$ respectively in response to operator instructions via control computer 9. They are then added in a summer 18 before being displayed. It will be understood that the factors $x/(x+y)$ and $y/(x+y)$ may be generated as required or a suitable number for expected requirements may be retained, for example in read-only-memory (ROM) 19, for withdrawal as requested by computer 9. The two factors are, of course, complementary. In the extreme the factors may have the value ½ or 1 and 0 only as in the FIG. 3 circuit described.

What I claim is:

1. Apparatus for displaying a representation of body sections for use, for example, in diagnostic X-ray apparatus including storage means for storing data signals representing the absorption coefficient of elements of two-dimensional spaced arrays of elements notionally delineated in respective spaced cross-sections of the body, means providing weighting functions, means for weighting data for corresponding elements of said first mentioned arrays with appropriate weighting functions to provide interpolated data signals according to predetermined interpolating functions said interpolated data signals representing coefficients for corresponding elements of another array of elements notionally delineated in another cross-section of said body intermediate the first mentioned body section and means for displaying a repesentation of any of said body sections.

2. An apparatus according to claim 1 wherein said storage means is divided into zones each having an independent input/output channel and including means for applying the data signals for adjacent pairs of said first mentioned arrays in diferent ones of said zones.

3. An apparatus according to claim 1 wherein said storage means is a video disc store.

4. An apparatus according to claim 1 wherein said other array is situated substantially midway between two of said first mentioned arrays.

5. An apparatus according to claim 1 arranged to display the said representations in a sequence related to their position in the body.

* * * * *